(12) United States Patent
Schechner et al.

(10) Patent No.: US 8,778,425 B2
(45) Date of Patent: Jul. 15, 2014

(54) COATED CHEWING GUM

(75) Inventors: Gallus Schechner, Ober-Ramstadt (DE); Carola Braunbarth, Rossdorf (DE); Tilo Poth, Weinheim (DE); Holger Franke, Ginsheim (DE); Lutz Guderjahn, Offstein (DE); Jörg Kowalczyk, Eisenberg (DE)

(73) Assignee: Sudzucker Aktiengesellschaft Mannheim, Ochsenfurt (DE)

( * ) Notice: Subject to any disclaimer, the term of this patent is extended or adjusted under 35 U.S.C. 154(b) by 1533 days.

(21) Appl. No.: 10/528,842

(22) PCT Filed: Sep. 13, 2003

(86) PCT No.: PCT/EP03/10213
§ 371 (c)(1),
(2), (4) Date: Jul. 26, 2005

(87) PCT Pub. No.: WO2004/028262
PCT Pub. Date: Apr. 8, 2004

(65) Prior Publication Data
US 2006/0034975 A1  Feb. 16, 2006

(30) Foreign Application Priority Data
Sep. 23, 2002 (DE) .................................. 102 48 632

(51) Int. Cl.
A23G 4/06  (2006.01)
(52) U.S. Cl.
USPC ............................................................ 426/5
(58) Field of Classification Search
USPC .................................................. 426/3, 4, 5, 6
See application file for complete search history.

(56) References Cited

U.S. PATENT DOCUMENTS

| 4,474,749 A | 10/1984 | Kruppa |
| 5,298,263 A * | 3/1994 | Yatka et al. ........................ 426/5 |
| 5,980,955 A | 11/1999 | Hubert et al. |
| 2001/0021373 A1 | 9/2001 | Greenberg et al. |
| 2001/0021403 A1 | 9/2001 | Greenberg et al. |
| 2003/0219388 A1* | 11/2003 | Kropf et al. ...................... 424/50 |

FOREIGN PATENT DOCUMENTS

| CA | 2 227 408 | 4/1997 |
| CH | 1198659 | 11/1998 |
| DE | 10063945 A1 * | 7/2002 ............... A61K 6/00 |
| EP | 0 091 611 | 10/1983 |
| EP | 0 263 224 | 4/1988 |
| EP | 0 414 932 | 3/1991 |
| JP | 2000-270810 | 10/2000 |
| JP | 2001/1299280 | 10/2001 |

OTHER PUBLICATIONS

Original Chinese and English translation of "Observation of effect of two kinds of chewing gum on cleaning dental plaque," Beijing Journal of Stomatology, vol. 3, No. 3, 1995.
International Search Report dated Jan. 21, 2004 corresponding to International Patent Application No. PCT/EP 03/10213.
English translation of Japanese Office Action corresponding to related Japanese Patent Application No. 2004-538900 dated Jul. 29, 2008.

* cited by examiner

Primary Examiner — Nikki H Dees
(74) Attorney, Agent, or Firm — Ostrolenk Faber LLP

(57) ABSTRACT

The invention relates to a chewing gum coated with at least one layer, the layer comprising slightly water-soluble calcium salt and/or a composite thereof.

38 Claims, No Drawings

COATED CHEWING GUM

CROSS REFERENCE TO RELATED APPLICATION

The present application is a 35 U.S.C. §371 national phase conversion of PCT/EP2003/10213 filed Sep. 13, 2003, which claims priority of German Application No. 10248632.8 filed Sep. 23, 2002.

TECHNICAL FIELD

The invention relates to a chewing gum which is coated by at least one layer, this layer comprising slightly water-soluble calcium salt and/or composites thereof.

BACKGROUND OF THE INVENTION

Food residues which remain in the mouth after eating are one of the main causes for the occurrence of caries. In most cases, cleaning the teeth after eating is simply omitted. In particular, the sugar present therein acts as nutrient for bacteria of the oral cavity which are responsible for the formation of caries, firstly by bacterial breakdown products (in particular organic acids, such as lactic acid, formic acid or acetic acid) and secondly by increased plaque formation.

Chewing chewing gum after eating is said to counter-act the formation of caries-promoting bacterial breakdown products. For this, in these chewing gums, what are termed sugar replacers, in particular sugar alcohols such as sorbitol, isomalt and xylitol, are used. Although the increased salivary flow prevents or at least reduces the formation of caries-causing acids, these chewing gums can improve general dental health only to a limited extent.

Tooth enamel and also the supporting tissue of bones consist predominantly of the mineral hydroxyapatite. The addition of calcium salts and/or phosphate salts to chewing gums is intended to serve for improving the remineralization of tooth enamel.

It is disadvantageous for these compositions that adding conventional ground, microcrystalline calcium salts and/or phosphate salts does not achieve sufficient remineralization of the tooth material.

SUMMARY OF THE INVENTION

It is the object of the present invention, therefore, to provide as an alternative a chewing gum which, in addition to a good taste, additionally has beneficial use for dental health during and/or shortly after its consumption.

This object is achieved by a chewing gum which is coated by at least one layer, this layer comprising slightly water-soluble calcium salt and/or composites thereof.

The inventive chewing gum consists of sugars and/or sugar alcohols, intense sweeteners, flavorings, other odor- and taste- or consistency-giving ingredients, colorings and a water-insoluble gum base becoming plastic on chewing. In addition, the chewing gums can also comprise release agents (for example talcum).

Gum bases are mixtures of consistency-giving substances, the natural gums, these are solidified saps (exudates) from tropical plants such as chicle, gum arabic, gutta-percha, gum karaya and tragacanth, rubber and the thermoplastics butadiene-styrene copolymers, isobutylene-isoprene copolymers, polyethylene, polyisobutylene, poly-(vinyl ester)s of unbranched fatty acids from $C_2$ to $C_{18}$, and poly(vinyl ether)s.

As plasticizers, use is made of resins and balsams. The natural substances include gum benzoin, dammar resin, colophony, mastic, myrrh, frankincense, Peru balsam, sandarac, shellac and Tolu balsam, the synthetic substances include coumarone-indene resin, glycerol pentaerythritol esters of the resin acids of colophony and hydrogenation products thereof.

To influence elasticity, use is made of paraffins (natural and synthetic) and also waxes. In the case of the waxes, there are those from the plant sector, such as carnauba wax and those of animal origin, such as beeswax or lanolin, in addition those from the mineral sector such as microcrystalline waxes, and also chemically modified or synthetic waxes. As plasticizers, use is made of emulsifiers (for example lecithins or mono- and diglycerides of edible fatty acids) and esters such as glycerol acetate and also glycerol.

To regulate the gum base consistency, plant hydro-colloids such as agar, alginic acid and alginates, guar seed meal, carob bean meal or pectin are added. For specific setting of the chewing properties of gum bases, fillers are used, these are carbonates of calcium or magnesium, oxides, for example aluminum oxide, silica and silicates of calcium or magnesium. Stearic acid and its calcium and magnesium salts are used to reduce the adhesion of the gum base to tooth enamel.

Before the remaining ingredients which are required according to the formula for producing chewing gum are mixed together, it is necessary to heat the gum base, which constitutes about 20-35% (but at least 15%) of the finished chewing gum, to 50-60° C.

By means of the chewing motion which is carried out, chewing gum promotes salivary flow. The caries-causing acids are diluted and thus the health of the oral cavity is supported in a natural manner.

Slightly water-soluble calcium salt is taken to mean those salts which, at 20° C., are soluble in water at less than 0.1% by weight (1 g/l). Such suitable salts are, for example, calcium hydroxyphosphate ($Ca_5[OH(PO_4)_3]$) or hydroxyapatite, calcium fluorophosphate ($Ca_5[F(PO_4)_3]$) or fluoroapatite, fluorine-doped hydroxyapatite of the composition $Ca_5(PO_4)_3(OH,F)$ and calcium fluoride ($CaF_2$) or fluorite or fluorspar, and also other calcium phosphates such as di-, tri- or tetracalcium phosphate ($Ca_2P_2O_7$, $Ca_3(PO_4)_2$, $Ca_4P_2O_9$, oxyapatite ($Ca_{10}(PO_4)_6O$) or non-stoichiometric hydroxyapatite ($Ca_{5-1/2(x+y)}(PO_4)_{3x}(HPO_4)_x(OH)_{1-y}$). Carbonate-containing non-stoichiometric apatite are likewise suitable (for example $Ca_{5-1/2(x+y+z)}(PO_4)_{3-x-z}(HPO_4)_x(CO_3)_z(OH)_{1-y}$), calcium hydrogen phosphate (for example $CaH(PO_4).2\ H_2O$) and octacalcium phosphate (for example $Ca_8H_2(PO_4)_6.5\ H_2O$).

A suitable mineralizing active compound is preferably a finely divided slightly water-soluble calcium salt which is selected from hydroxyapatite, carbonate-containing non-stoichiometric apatite, fluoroapatite, fluorine-doped hydroxyapatite and mixtures thereof. These calcium salts can deposit best on the tooth material and effect mineralization of same.

Composite materials are taken to mean composites which comprise a slightly water-soluble calcium salt and also other components and aggregates appearing microscopically heterogeneous but macroscopically homogeneous.

The finely divided calcium salts or the finely divided calcium salt primary particles present in the composite materials can also be coated by one or more surface-modification agents.

By this means, for example, the production of composite materials can be facilitated in those cases in which the nanoparticulate calcium salts are dispersed with difficulty. The surface-modification agent is adsorbed to the surface of the nanoparticles and changes it in such a manner that the dispersibility of the calcium salt increases and the agglomeration of the nanoparticles is prevented.

Furthermore, a surface modification can influence the structure of the composite materials and also the loading of further components with the nanoparticulate calcium salt. In this manner, when the composite materials are used in mineralization processes, it is possible to affect the course and rate of the mineralization process.

Surface-modification agents are taken to mean substances which adhere physically to the surface of the finely divided particles, but do not chemically react with these. The individual molecules of the surface-modification agents which are adsorbed or bound to the surface are essentially free from intermolcular bonds. Surface-modification agents are taken to mean, in particular, dispersants. Dispersants are known to those skilled in the art under the terms surfactants and protective colloids. Suitable surfactants or polymeric protective colloids can be found in German application DE 198 58 662 A1.

The inventive composite materials in which the primary particles of the calcium salts are surface modified can be produced by similar precipitation methods as described above, but with the precipitation of the nanoparticulate calcium salts or of the composite materials taking place in the presence of one or more surface-modification agents.

The layer which coats the chewing gum and comprises the slightly water-soluble calcium salt advantageously leads to the calcium salt being able to be released more easily than in the case of the direct incorporation of the salts into the chewing gum mass, in which the calcium salts which are incorporated remain firmly bonded to the sticky matrix of the gum base. The layer coating the chewing gum dissolves very rapidly on chewing in the mouth and can in this way make the necessary amount of active compound available in the mouth which advantageously ensures effective mineralization of the teeth. The addition of the calcium salts and/or composites thereof does not affect the crunch, that is to say the crispiness, of the chewing gums.

According to a particular embodiment, the layer coating the inventive chewing gum comprises sugars and/or sugar alcohols.

Advantageously, the layer comprising sugars and/or sugar alcohols dissolves particularly rapidly in the mouth. In addition to the sweet taste experience, it can also be applied particularly well to a chewing gum core.

Despite the in-part cariogenic constituents (sugars), consumption of the inventive chewing gums leads, in addition to the consumption experience, to teeth cleaning and teeth care and also, moreover, to mineralization of the tooth enamel and/or dentine. The teeth cleaning which has previously been necessary to keep the teeth healthy, but has not always been possible after eating, customarily using toothbrush, toothpaste and/or mouthwash, can thus be dispensed with without harm for the teeth.

The inventive addition of slightly water-soluble calcium salts and/or composites thereof in chewing gums comprising sugar replacers effects mineralization of the teeth during and/or after consumption of the chewing gum and thus contributes particularly to the maintenance of healthy teeth. Advantageously, the sugar alcohols, owing to their physico-chemical properties, are particularly suitable for preparing thin layers, especially in the dragee process. Particular preference is given to the use of isomalt in the coating layer, since this sugar alcohol has a comparatively high glass transition temperature which particularly facilitates processing.

The layer coating the chewing gum can be produced in various ways, for example by multiple immersion of the chewing gum core into an appropriate solution and/or dispersion.

DETAILED DESCRIPTION OF THE INVENTION

According to a preferred embodiment of the invention, the layer coating the chewing gum is a dragee-coated layer, that is to say the layer is applied to the chewing gum in the dragee-coating method. The dragee layer (coat) consists of a smooth or rippled comprising sugars and/or sugar alcohols, types of chocolate and/or other glazings which is applied around a liquid, soft or solid core by means of the dragee-coating method.

In the dragee-coating method, for example a saturated sugar solution is sprayed in finely divided form from a nozzle onto the core rotating in dragee kettles. The sugar crystallizes owing to the hot air which is blown in at the same time and gradually forms many thin layers around the core. If the sugar layer contains no residual moisture, it is termed a hard dragee, and in the case of soft dragees, in contrast, approximately 6 to 12% by weight, in particular 8 to 10% by weight, residual moisture can be present. Dragees are frequently externally provided with a thin release layer and gloss layer, the gloss layer being produced by treatment with waxy substances, for example carnauba wax. In particular, use is made of substances influencing characteristics, for example starch, and also coloring, odor- and taste-giving substances.

According to a preferred embodiment, the sparingly or slightly water-soluble calcium salt present in the coating layer has a particle size or particle fineness less than 1000 nm. Particle fineness is to be taken to mean here the diameter of the particles in the direction of their greatest length. The mean particle fineness relates to a volume-averaged value. The inventive nanoparticles have a higher surface/volume ratio than the microcrystalline particles and are distinguished by a higher reactivity compared with these.

They can therefore be used better for remineralizing demineralized tooth material. Remineralizing in this context is taken to mean the redeposition of ions in bone material, that is to say the filling in of gaps within the existing hard tooth tissue such as enamel and dentine.

Surprisingly, it has further been found that by adding the slightly water-soluble calcium salt and/or composites thereof in addition, new layers of a biomimetic material can form on the tooth. This material is chemically and structurally very similar to the natural hard tooth tissue. Therefore, it is not only gaps within the crystal structure that are compensated for, as takes place in the remineralization of the tooth material, but also new material which adheres to the tooth and is dentine-like in its nanostructure is produced. This new formation of biomimetic material is termed hereinafter neomineralization. In the inventive context the term mineralization comprises not only remineralization but also neomineralization.

According to a preferred embodiment, the sparingly or slightly water-soluble calcium salt has a particle size or particle fineness of 5 to 300 nm, in particular 5 to 100 nm. An advantage of these particularly low particle sizes or particle finenesses is that these primary particles exhibit particularly effective remineralization of the teeth and, moreover, have the ability to form new, neomineralized layers of material very similar to the hard tooth tissue.

According to a particularly preferred embodiment, the inventive calcium salts have an elongate shape, in particular rod shape or needle-like shape. This has the particular advantage that they are very similar to the shape of the biological apatites (for example bone apatites or dentine apatites) and therefore have a particularly good capability for remineralization and neomineralization. Such calcium salts may be produced, for example, in the form of rod-shaped primary particles by the method disclosed by DE 198 58 662 A1.

According to a preferred embodiment, 0.001 to 5% by weight of slightly water-soluble calcium salt and/or composites thereof are present. Preference is given to use of 0.01 to 2% by weight, and in particular 0.1 to 1% by weight, calcium salt and/or composites thereof in the layer coating the chewing gum.

According to a preferred embodiment, the coating layer of an inventive chewing gum comprises a composite of a slightly soluble calcium salt with a protein component.

Proteins can be adsorbed to the surface of the nanoparticles, as a result of which a composite material of protein and slightly water-soluble calcium salt is formed. In particular, by means of the adsorbed proteins, coagulation and agglomeration of the calcium salts is also prevented and the crystal growth is retarded. In the case of mineralization of a tooth, and in particular in the case of neomineralization, it is of great advantage if no uncontrolled crystal growth takes place which could only form a loose crystal structure. By means of the protein backbone, the crystal growth can proceed in a braked and controlled manner. Thus, a particularly tight and solid crystal structure is formed.

Surprisingly, it has been found that the slightly water-soluble calcium salts and, in particular, the composites of slightly water-soluble calcium salt with proteins, in addition to remineralization of the tooth, are also able to reduce the extent of relatively large damage in tooth dentine and/or tooth enamel by the formation of completely new crystals.

In the natural formation of bone material, for example tooth enamel and tooth dentine, a protein matrix causes the ordered deposition of hydroxyapatite in the tooth or bone, which protein matrix principally consists of collagen and also other proteins. With the composites of slightly soluble calcium salt and proteins, the neomineralization proceeds in a similar manner to biomineralization and thus leads to a particularly beneficial effect on tooth health when the inventive chewing gum is consumed.

The protein component preferably present in the composite is selected in particular from proteins, protein breakdown products and derivatives of proteins or protein breakdown products.

Proteins which come into consideration here are all proteins independently of their origin, that is to say not only animals proteins, but also plant proteins. Suitable animal proteins are, for example, collagen, fibroin, elastin, keratin and albumin. Suitable plant proteins are, for example, wheat products and wheat germ products (gluten), rice protein, soybean protein, oat protein, pea protein, almond protein and potato protein. Single-cell proteins, for example yeast protein or bacterial proteins, are also suitable.

Inventively preferred proteins are animal proteins such as collagen and keratin. However, the protein can likewise be selected from a plant source or marine source.

Protein breakdown products are taken to mean those products which are obtainable by hydrolytic, oxidative or reductive breakdown of water-insoluble proteins to give oligopeptide and polypeptide structures having lower molecular weight and having an improved water solubility.

The hydrolytic breakdown of water-insoluble proteins is the most important breakdown method; it can proceed under the catalytic influence of acids, alkalis or enzymes. Those which are preferably suitable are, especially, those protein breakdown products which are not broken down further than is required to achieve the water solubility.

The less broken-down protein hydrolyzates comprise, for example, gelatin, which is preferred in the context of the present invention, and which can have molar masses in the range from 15 000 to 400 000 D. Gelatin is a polypeptide which is principally produced by hydrolyzing collagen under acidic or alkaline conditions. Particular preference is given to gelatin produced under acidic or strongly acidic conditions. The gel strength or gelatin is proportional to its molecular weight, that is to say a more strongly hydrolyzed gelatin gives a less viscous solution. The gel strength of gelatin is reported in Bloom values. In the enzymatic cleavage of gelatin the polymer size is greatly reduced which leads to very low Bloom values.

Derivatives of proteins and protein breakdown products are taken to mean chemically modified proteins or protein hydrolyzates which are obtainable, for example, by acylation of free amino groups, by addition of ethylene oxide or propylene oxide and hydroxyl, amino or carboxyl groups or by alkylation of hydroxyl groups of the protein or protein breakdown product or of a hydroxyalkyl derivative thereof, for example with epoxypropyltrimethylammonium chloride or 3-chloro-2-hydroxypropyltrimethylammonium chloride.

In a particularly preferred embodiment, the protein component is selected from gelatin, hydrolyzates thereof and mixtures thereof. Preferably, a protein component should be present in an amount of at least 1% by weight, preferably 1 to 50, in particular 20 to 40% by weight.

In the inventive composites, the primary particles of the calcium salts are associated to the backbone of the protein component. The proportion of the protein components in such composite materials is between 0.1 and 50% by weight, but preferably between 1.0 and 45% by weight, in particular 20 to 40% by weight, based on the weight of the composite material.

Suitable materials are particularly hydroxyapatite nanoparticles which have a clearly discernible crystalline morphology, the particle fineness of which is therefore in the range from 5 to 300 nm. Those which are likewise suitable are composite materials in which the finely divided slightly soluble calcium salts having particle finenesses of 5 to 300 nm together with finely divided proteins, protein hydrolyzates or derivatives thereof form a spatial structure in such a manner that the finely divided calcium salts lie on the protein structure and quasi spatially reproduce these. Composite materials which consist of such preferably suitable nanoparticulate calcium salts and protein components lead to particularly good mineralization of the teeth on consumption of the inventive chewing gum.

Slightly water-soluble calcium salts can add to the protein chains particularly readily in rod form. This leads to a markedly improved cohesion of the composite material. Materials which are suitable in particular here are primary particles having a particle fineness of 5 to 300 nm, and preferably 5 to 100 nm, since these particularly small crystallites are very similar to the shape of biological apatites and, because of the small size, can also add still better to the protein chains. These composites lead as a result to a particularly effective mineralization of teeth.

Inventively suitable composite materials can be produced by precipitation from aqueous solutions of water-soluble calcium salts with aqueous solutions of water-soluble phosphate and/or fluoride salts in the presence of protein components by various methods as are already described in German patent application DE 199 30 335.

For production of the inventive chewing gums, the active compound, that is to say the finely divided, slightly water-soluble calcium salt and/or composites thereof, preferably the composite material of the slightly soluble calcium salt and a protein component, is simply added to a solution and/or dispersion from which the layer is produced, and stirred.

In a preferred embodiment of the present invention, the inventive chewing gum is a sugar-containing chewing gum. In the context of the present invention, "sugar" or "sugars" is taken to mean products such as sucrose, purified crystalline sucrose, for example in the form of refined sugar, raffinates, refined white sugar, white sugar or semi-white sugar, aqueous solutions of sucrose, for example in the form of liquid sugar, aqueous solutions of sucrose partially inverted by hydrolysis, for example invert sugar, syrup or invert liquid sugar, glucose syrup, dried glucose syrup, dextrose containing water of crystallization, dextrose free of water of crystallization and other starch saccharification products and also trehalose, trehalulose, tagatose, lactose, maltose, fructose, leucrose, isomaltulose (palatinose), condensed palatinose and hydrogenated condensed palatinose. The inventive sugar-containing chewing gum is therefore characterized in that either the chewing gum itself, or the coating layer or both, comprise, as sweetener, sucrose, invert liquid sugar, invert sugar syrup, glucose, glucose syrup, polydextrose, trehalose, trehalulose, tagatose, lactose, maltose, fructose, leucrose, isomaltulose (palatinose), condensed palatinose, hydrogenated condensed palatinose or mixtures thereof. The inventive sugar-containing chewing gum can, in addition to the above-mentioned sugars, also comprise sugar replacers, in particular sugar alcohols such as lactitol, sorbitol, xylitol, mannitol, maltitol, erythritol, 6-O-α-D-glucopyranosyl-D-sorbitol (1,6-GPS), 1-O-α-D-glucopyranosyl-D-sorbitol (1,1-GPS), 1-O-α-D-glucopyranosyl-D-mannitol (1,1-GPM), maltitol syrup, sorbitol syrup, fructooligosaccharides or mixtures thereof and also mixtures of sugar alcohols and sugars.

In a further preferred embodiment of the invention, the inventive chewing gum is a sugar-free chewing gum. In the context of the present invention, a "sugar-free chewing gum" is taken to mean a chewing gum in which not only the chewing gum itself, but also the coating layer, comprises as sweetener none of the above-mentioned sugars, that is to say neither sucrose, invert liquid sugar, invert sugar syrup, dextrose, glucose syrup, trehalose, trehalulose, tagatose, lactose, maltose, fructose, leucrose, isomaltulose (palatinose), condensed palatinose, hydrogenated condensed palatinose, nor mixtures thereof, but sugar replacers. In a preferred embodiment of the invention, the inventive sugar-free chewing gum is a chewing gum which has a maximum content of the above-mentioned sugars of 0.5% by weight, based on the dry weight.

The term "sugar replacers" comprises all substances apart from the above-mentioned sugars which can be used for sweetening foods. The term "sugar replacers" comprises, in particular, substances such as hydrogenated mono- and disaccharide sugar alcohols, for example lactitol, xylitol, sorbitol, mannitol, maltitol, erythritol, isomalt, 1,6-GPS, 1,1-GPS, 1,1-GPM, sorbitol syrup, maltitol syrup, and also fructooligosaccharides. Preferably, the inventive sugar-free chewing gums are therefore characterized in that not only the chewing gum itself but also the coating layer comprises as sweetener lactose, maltose, fructose, leucrose, palatinose, condensed palatinose, hydrogenated condensed palatinose, fructooligosaccharides, lactitol, sorbitol, xylitol, mannitol, maltitol, erythritol, 1,6-GPS, 1,1-GPS, 1,1-GPM, sorbitol syrup, maltitol syrup or mixtures thereof. Those which are preferred according to the invention are sugar alcohols such as sorbitol or sorbitol syrup, mannitol, xylitol, lactitol, maltitol or maltitol syrup, 1,1-GPS, 1,6-GPS, 1,1-GPM or mixtures thereof.

Sugar alcohols have the advantage that they contain fewer calories per 100 g and that, furthermore, they are broken down only very slowly, or not at all, by bacteria of the oral flora to give acids, so that they are not cariogenic.

A preferably used mixture of 1,6-GPS and 1,1-GPM is isomalt, in which 1,6-GPS and 1,1-GPM are present in equimolar or virtually equimolar amounts. According to the invention, in the inventive chewing gums, in particular sugar-free chewing gums, not only in the chewing gum itself, but also in the layer coating it, use can likewise be made of 1,6-GPS-enriched mixtures of 1,6-GPS and 1,1-GPM having a 1,6-GPS content of 57% by weight to 99% by weight and a 1,1-GPM content of 43% by weight to 1% by weight, 1,1-GPM-enriched mixtures of 1,6-GPS and 1,1-GPM having a 1,6-GPS content of 1% by weight to 43% by weight and a 1,1-GPM content of 57% by weight to 99% by weight, and also mixtures of 1,6-GPS, 1,1-GPS and 1,1-GPM as sweetener. 1,6-GPS-enriched mixtures and 1,1-GPM-enriched mixtures of 1,6-GPS and 1,1-GPM are disclosed in DE 195 32 396 C2, the disclosure of this publication with respect to the description and preparation of the 1,6-GPS-enriched and 1,1-GPM-enriched sweetener mixtures being incorporated in full by reference into the contents of the disclosure of the present teaching. 1,1-GPS-enriched mixtures of 1,6-GPS and 1,1-GPM are disclosed, for example, in EP 0 625 578 B1, the contents of the disclosure of this publication with respect to the description and preparation of the 1,1-GPS-, 1,6-GPS- and 1,1-GPM-containing sweetener mixtures being incorporated in full by reference into the contents of the disclosure of the present teaching.

A further inventively preferred mixture which can be used in the inventive chewing gums, in particular sugar-free chewing gums, is a syrup having a dry matter of 60 to 80%, consisting of a mixture of hydrogenated starch hydrolyzate syrup and isomalt powder or isomalt syrup, the dry matter of the syrup being of 7 to 52% (weight/weight) 1,6-GPS, 24.5 to 52% (weight/weight) 1,1-GPM, 0 to 52% (weight/weight) 1,1-GPS, 0 to 1.3% (weight/weight) sorbitol, 2.8 to 13.8% (weight/weight) maltitol, 1.5 to 4.2% (weight/weight) maltotriitol and 3.0 to 13.5% (weight/weight) higher polyols. Such a syrup is disclosed in EP 1 194 042 B1, the contents of the disclosure of this publication with respect to the description and preparation of the syrup consisting of a mixture of hydrogenated starch hydrolyzate syrup and isomalt powder or isomalt syrup being incorporated in full by reference into the contents of the disclosure of the present teaching.

The inventive sugar-free chewing gum which is coated by at least one layer which comprises a slightly water-soluble calcium salt and/or composites thereof can be, for example, a hard-coated sugar-free chewing gum which comprises a sugar-free chewing gum core and a sugar-free hard coating, which comprises an essentially hygroscopic sugar-free sweetener, the chewing gum core having a water content of less than about 2.5% by weight, based on the weight of the core. The essentially hygroscopic sweetener can be, for example, sorbitol or hydrogenated isomaltulose. Such sugar-free hard-coated chewing gums are described in WO 88/08671, the contents of the disclosure of this publication with respect to the description and preparation of the hard-coated sugar-free chewing gums being incorporated in full by reference into the contents of the disclosure of the present teaching.

In a further embodiment of the invention, it is provided that not only the inventive sugar-containing chewing gums, but also the inventive sugar-free chewing gums can additionally comprise, in the chewing gum itself and/or in the layer coating it, in addition to the above-mentioned sugars and/or sugar replacers, one or more intensive sweeteners. Intensive sweeteners are compounds which are distinguished by an intensive sweet taste, with a low, or negligibly low, nutritional value. According to the invention, it is provided, in particular, that the intensive sweetener used in the inventive chewing gums is cyclamate, for example sodium cyclamate, saccharin, for example saccharin sodium, Aspartame®, glycyrrhizin, neohesperidin dihydrochalcone, thaumatin, monellin; acesulfame, stevioside, alitame, sucralose, or a mixture thereof. When such intensive sweeteners are used, in particular the proportion of sugars can be reduced and nevertheless the predominantly sweet taste can be retained.

In a further embodiment of the invention, it is provided that the inventive chewing gum not only has a coating layer, in particular dragee-coated layer, which comprises a slightly soluble calcium salt and/or composites thereof, but at least 2 to about 100 of such coating layers, in particular dragee-coated layers. According to the invention, it is possible that the individual layers have the same sweetener, or the same sweeteners. Obviously, according to the invention there is also the possibility that the individual layers can also comprise different sweeteners. Such dragee-coated chewing gum products are therefore coated by layer sequences of different sweetener composition. By a suitable choice of the sequence and number of the coating steps with the different sweeteners, chewing gums of desired properties can be specifically produced.

For example, the inventive chewing gum can first be coated with 1 to about 45 dragee-coated layers which comprise the 1,1-GPM-enriched mixture of 1,6-GPS and 1,1-GPM. Then, onto these layers, 1 to about 45 layers of the 1,6-GPS-enriched mixture of 1,6-GPS and 1,1-GPM are applied. A dragee-coated chewing gum of this type is distinguished, owing to the high solubility and greater sweetening power of the 1,6-GPS-enriched mixture forming the outer layer by an overall higher sweetening power compared with, for example, hydrogenated isomaltulose-coated chewing gums. A layer sequence of this type is described in DE 195 32 396 C2, the contents of the disclosure of this publication with respect to the description and production of chewing gums having this layer sequence being incorporated in full by reference into the contents of the disclosure of the present teaching.

For example, the inventive chewing gum can be a hard-coated chewing gum, the dragee coats having a plurality of layers which comprise about 50% to about 100% xylitol, and a plurality of layers which comprise about 50% to about 100% hydrogenated isomaltulose. Such chewing gums are disclosed in WO 93/18663, the contents of the disclosure of this publication with respect to the description and preparation of chewing gums having this layer sequence being incorporated in full by reference into the contents of the disclosure of the present teaching.

In a further embodiment it is provided that the individual dragee-coated layers coating the chewing gum comprise the same calcium salt and/or the same composites thereof. According to the invention, however, it is obviously also possible that the individual layers which coat the chewing gum comprise different calcium salts and/or different composites thereof. Obviously, there is also the possibility that individual layers comprise no calcium salt or no composites thereof.

According to a further preferred embodiment, the chewing gum, in addition to the slightly water-soluble calcium salt and/or composites thereof, additionally comprises at least one fluoride salt. Surprisingly, it has been found that the addition of fluoride leads to a synergistic amplification of the nucleating effect of the slightly soluble calcium salts and/or composites thereof. In particular, preference is given to the addition of sodium fluoride and/or potassium fluoride. In the case of simultaneous addition of slightly water-soluble calcium salt and small amounts of fluoride, an about five-fold synergistic amplification is demonstrated. Preference according to the invention is given to amounts of 0.05 to 0.15% by weight, in particular 0.08 to 0.12% by weight, fluoride salt.

According to a further preferred embodiment, the chewing gum comprises flavorings, fillers and/or further aids (for example glycerol or mineral salts, for example $Zn^{2+}$ or $Mg^{2+}$).

In principle, any natural or nature-identical flavorings can be used. Particularly preferably, use can be made, in particular, of flavoring oils, for example peppermint oil, spearmint oil, eucalyptus oil, aniseed oil, fennel oil, cumin oil and synthetic flavoring oils.

Fruit flavorings can also be present, in particular in solid or liquid fruit preparations, fruit extracts or fruit powders. Preference is given here to pineapple, apple, apricot, banana, blackberry, strawberry, grapefruit, bilberry, raspberry, maracuja, orange, sour cherry, redcurrant and blackcurrant, woodruff and lemon.

Active compounds, for example menthol and/or vitamins, can also be present in the inventive chewing gum. Likewise, organophosphonates, for example 1-hydroxyethane-1,1-diphosphonic acid, phosphonopropane-1,2,3-tricarboxylic acid (Na salt) or 1-azacycloheptane-2,2-diphosphonic acid (Na salt), and/or pyrophosphates can be added which reduce the formation of tartar. The inventive chewing gums can also comprise acetylsalicylic acid as active compound.

As preservatives, use can be made of all preservatives permitted for foods, for example sorbic acid or benzoic acid and derivatives thereof, for example sodium benzoate and parahydroxybenzoate (sodium salt), sulfur dioxide or sulfurous acid, sodium nitrite or potassium nitrite. Colorings and pigments to achieve an attractive appearance can likewise be present.

The present invention likewise relates to a method for producing chewing gums which are coated by at least one layer which comprises at least one slightly water-soluble calcium salt and/or one or more composites thereof. The inventive method for producing the inventive chewing gums comprises producing a chewing gum core and coating the chewing gum core with at least one layer which comprises a slightly water-soluble calcium salt and/or a composite thereof.

According to the invention it is provided that the chewing gum core can be produced by customary methods. After producing the chewing gum cores, the finished chewing gum cores are preferably dragee-coated, with dragee-coating methods which are customarily used being able to be used. For example, the finished chewing gum cores can be subjected to a soft dragee coating, a hard dragee coating or a suspension dragee coating. A "soft dragee coating" is taken to mean the application of saccharides dissolved in water to moving cores, in particular chewing gum cores, with, after each application, a saccharide powder being dispersed on to bind the moisture. This type of dragee coating produces a soft dragee coating. A "hard dragee coating" is likewise taken to mean, as in the soft dragee coating, the application of saccharides dissolved in water onto moving chewing gum cores, but with no saccharide powder being applied, but rather the non-aqueous constituents being dried on immediately. As in the soft dragee coating, a multiplicity of different individual applications are carried out, between which drying is performed with warm air or cold air, so that dragee coatings of different thicknesses can be produced. The hard dragee-coating method can also be carried out using two or more different saccharide solutions which are applied successively. In the "suspension dragee coating", the suspended mixture consists of a liquid phase which, for example, comprises sugars or sugar replacers dissolved in water, and also a solid phase which consists of fine crystalline parts of sugars and/or sugar replacers. The separate use of different saccharides is characteristic of this type of suspension dragee coating.

In a preferred embodiment of the inventive method, the chewing gum core is coated, by means of at least one hard dragee-coating step, with the layer comprising the calcium salt and/or composite thereof. The hard dragee-coating step comprises applying a solution or suspension which comprises at least one sweetener and the calcium salt and/or composites thereof, and subsequently drying the applied solution or suspension.

In a further embodiment of the inventive method, the chewing gum core is coated, by means of at least one soft dragee-coating step, with the layer comprising the calcium salt and/or composite thereof. The soft dragee-coating step comprises applying a solution or suspension which comprises at least one sweetener and dusting the applied solution or suspension with a sweetener powder. In a development, the applied solution or suspension comprises the total amount of the calcium salt and/or composites thereof or a part thereof. That is to say, in this development the calcium salt and/or its composite is completely or partially introduced into the solution or suspension and, together with this, is applied to the chewing gum cores to be dragee-coated. In a further development, the sweetener powder comprises the total amount of the calcium salt and/or composites thereof or a part thereof. That is to say, in this development, the calcium salt and/or its composite is completely or partially used together with the sweetener powder for dusting the solution or suspension applied to the chewing gum core.

According to the invention, it is provided that the hard dragee-coating or soft dragee-coating steps can be repeated several times, so that the chewing gum cores are provided in each case with a plurality of coating layers.

The slightly water-soluble calcium salt is, according to the invention, selected from fluoroapatite, carbonate-containing non-stoichiometric apatite, hydroxyapatite and fluorine-doped hydroxyapatite, the calcium salt having in particular a particle size less than 1000 nm, preferably 5 to 300 nm.

The coating layer comprises 0.001 to 5% by weight, preferably 0.01 to 2% by weight, of calcium salt and/or a composite thereof.

The present invention further relates to the use of a chewing gum which is coated by a layer which comprises slightly water-soluble calcium salt and/or composites thereof, for dental hygiene and dental care and also, furthermore, for mineralizing the tooth enamel and/or the dentine. Caries of the teeth can be effectively counteracted by chewing the inventive chewing gum. In addition to the eating pleasure, it is possible, in addition, to use the inventive chewing gum for caries prophylaxis.

EXAMPLES

The examples hereinafter are intended to describe the invention without restricting it thereto:

Example 1

1. Production of an Apatite-Protein Composite:

To produce the apatite-gelatin composite, 2000 ml of demineralized water are placed in a 4 l glass beaker thermostated to 25° C., in which 44.10 g (0.30 mol) of $CaCl_2.2H_2O$ (Fisher Chemicals p.a.) are dissolved. Separately from this, 35 g of gelatin (type A, DGF-Stoess, Eberbach) are dissolved in 350 ml of demineralized water at about 50° C. Both solutions are combined and vigorously stirred with a propeller agitator. The pH is set to 7.0 using dilute aqueous base.

To this gelatin and calcium salt solution are added evenly by pumping, using an automated feed setup, with vigorous stirring in the course of 120 min, 300 ml of a 0.6 M $(NH_4)_2HPO_4$ solution which had previously been set to pH 7.0. The pH is held constant at pH 7.0 by controlled addition of dilute aqueous base. After completion of the addition, the solution is further stirred over 24 h.

The dispersion is then charged into centrifuge tubes and the solids content separated from the solution by centrifugation. By extracting the residue five times by shaking into demineralized water and then renewed centrifugation, the salts are substantially extracted, so that chloride is no longer detectable.

2. Production of the Gum Base:

The base mass is preheated to 50° C. and the double-sigma blade kneader is thermostated to 40° C. Half the amount of sorbitol, the solid mannitol, the base mass and the lecithin are kneaded together for 5 minutes. Then half of the glycerol is added. After a further 5 minutes, a quarter of the sorbitol and half of the glycerol are added. After kneading for a further minute, one quarter of the amount of sorbitol and the other half of the glycerol are added. This mass is kneaded for a further 5 minutes before the maltitol syrup is added. Finally, after a further 5 minutes the Optamint® is added to the mass. This is kneaded for a further 5 minutes.

The mass is dusted with talcum and, still in the warm state, rolled out to 1.5 mm thickness. From these slabs, strips are cut. The cut slabs weigh about 2.5 to 4.0 g and are brought into a round shape by pressing or by rotation. The chewing gum cores thus produced are then subjected to the dragee coating.

TABLE 1

| Gum base | |
|---|---|
| Constituents | Amount |
| Chewing gum base mass Balear ®-T (Cafosa, Spain) | 33 g |
| D-sorbitol (98% pure, Aldrich) | 57.50 g |
| Mannitol powder (ABCR Chemikalien, Karlsruhe) | 5.00 g |
| Maltitol syrup (85% by weight) in water (HDS-Chemie, Austria) | 3.00 g |
| Glycerol, anhydrous (Merck) | 2.00 g |
| Optamint ® (Haarmann & Reimer GmbH) | 1.80 g |
| Lecithin (ACROS Organics) | 0.50 g |

A saturated solution is prepared at 40° C. (residue is filtered off) from 250 g of sucrose and 40 ml of water. To the solution are added 2.5 g of apatite-gelatin composite particles. The dragee kettle having 50 cm diameter is likewise heated to 40° C. and rotated. 500 g of chewing gum are added in portions, with it being necessary to take care that this material is not introduced too rapidly, to prevent sticking. The sugar solution is then sprayed in in the course of 5 h.

A corresponding dragee coating is also carried out using saturated solutions of the sugar replacers maltitol, sorbitol or isomalt under otherwise identical conditions.

Example 2

Production of Hard/Soft-Dragee-Coated Chewing Gums

As described in example 1, chewing gum cores are produced and then subjected to a hard/soft dragee coating. Dragees having a coat proportion of 33% by mass are produced.

1. Formula for Dragee Layer

| RAW MATERIALS | % |
| --- | --- |
| ISOMALT ST-M | 0.60 |
| Water | 0.40 |
| Maltitol syrup | 96.5 |
| Menthol flavoring (Haamann-Reimer, Holzminden, Germany) | 0.5 |
| Apatite-gelatin composite according to example 1 | 1.00 |
| Titanium dioxide | 1.00 |
| ISOMALT SF-PF | for dusting |

2. Preparation of the Dragee-Coating Solution

Isomalt ST-M (isomalt in which 1,6-GPS and 1,1-GPM are present in essentially equimolar amounts and which has a medium grain size, the diameter of approximately 90% of all particles being <3 mm) is dissolved with stirring in hot water and is mixed with the maltitol syrup. Apatite-gelatin composite particles which are produced as described in example 1, menthol flavoring and $TiO_2$ are then added to the solution. The resultant solution is held at 30 to 60° C. during the dragee-coating process to achieve better distribution of the solution on the chewing gum cores. The ratio of the isomalt solution to the maltitol syrup can vary between 100:0 and 1:99, depending on the desired coat hardness.

3. Dragee-Coating Process

In the first cycle, an application rate of 10-12 ml or 12.5-15.6 g of solution/kg of chewing gum cores is applied, the chewing gum cores being completely moistened. Thereafter the solution is thoroughly distributed. Then, dusting is carried out with isomalt ST-PF (5-8 g/kg of chewing gum cores) until the surface is dry. Isomalt ST-PF is characterized in that 1,6-GPS and 1,1-GPM are present in essentially equimolar amounts, a powder-fine grain size being present (diameter of approximately 90% of all particles <100 μm).

This procedure is repeated in the next three cycles using somewhat reduced amounts of solution and powder. Thereafter, further cycles are carried out, increasing amounts of solution and powder being used, until the desired final weight is virtually achieved. The surface of the dragee-coated chewing gum cores is then smoothed with small solution applications without addition of powder. Thereafter a polishing process is carried out, approximately 15 g of carnauba wax being crushed between the dragees. To avoid the dragee coat from breaking off during the polishing process, the speed of rotation of the drum is set very low at the start of the polishing process. As soon as the polishing medium is well distributed, the speed of rotation is increased.

In a modification of the method, a solution of maltitol syrup, isomalt ST-M, flavorings and colorings is prepared. To this solution is then added a portion of the amount provided of the apatite-gelatin composite particles produced according to example 1. This solution is then, as described above, applied to the chewing gum cores. Thereafter, dusting is carried out using a powder mixture which comprises isomalt ST-PF and the remaining amount of the apatite-gelatin composite particles to be incorporated into the dragee layer. In a further modification of the method, a solution is first prepared and applied to the chewing gum cores, which solution comprises maltitol syrup, isomalt ST-M, flavorings and colorings, but not the apatite-gelatin composite particles. After the application of this solution to the chewing gum cores, dusting is then carried out using either a powder mixture of isomalt ST-PF and the apatite-gelatin composite particles to be incorporated into the dragee layer, or only the apatite-gelatin composite particles (as what is termed "dry charge") in dry form.

Example 3

Soft Dragee Coating of Chewing Gum Cores

The chewing gum cores produced in example 1 are subjected in this example to a soft dragee coating. Dragees having a coat proportion of 33% by mass are produced.

1. Formula for Dragee Layer

| RAW MATERIALS | % |
| --- | --- |
| Maltitol syrup | 97.5 |
| Menthol flavoring (Haamann-Reimer, Holzminden, Germany) | 0.5 |
| Titanium dioxide | 1 |
| ISOMALT SF-PF | for dusting |
| Apatite-gelatin composite according to example 1 | 1 |

2. Pretreatment of Maltitol Syrup

So that the maltitol syrup distributes better on the chewing gum cores to be dragee-coated, the syrup, before the dragee coating, is heated to temperatures of about 40° C. to 50° C.

3. Dragee-Coating Process

The dragee-coating process is carried out as described in example 2.

Here also, the method can be modified by adding a portion of the apatite-gelatin composite particles to be incorporated into the dragee layer to the maltitol syrup and using the remaining amount of the apatite-gelatin composite particles in dry form either alone or together with the isomalt ST-PF powder for dusting. In a further modification of the method, the maltitol syrup is applied to the chewing gum cores without the apatite-gelatin composite particles. The total amount of the apatite-gelatin composite particles to be incorporated into the dragee layer is then used in dry form for dusting.

4. Pregumming

In soft dragee coating, pregumming can be performed. The pregumming can be carried out as follows:

1) first, a gum arabic solution (40% strength) and an isomalt solution (60% strength) in a ratio of 1:1 is applied to the non-dragee-coated chewing gum cores and isomalt ST-PF is then used for dusting or 2) a gum arabic solution (25-40% strength) is applied to the non-dragee-coated chewing gum cores and isomalt ST-PF is then used for dusting or 3) a gum arabic solution (25-40% strength) is applied and then only gum arabic is used for dusting.

Usually, 1 to 4 pregumming cycles are carried out. Before the dragee coating, the pregummed chewing gum cores are dried well, preferably intermediate storage overnight in dry surroundings being performed.

Example 4

Dragee Coating Using an Isomalt GS Solution

Dragees having a coat proportion of 33% by mass are produced.

1. Formula for Dragee Layer

| RAW MATERIALS | % |
| --- | --- |
| ISOMALT GS | 65.00 |
| Apatite-gelatin composite according to example 1 | 1.00 |
| Water | 28.80 |
| Aspartame | 0.05 |
| Acesulfame K | 0.05 |
| Gum arabic 50% | 4.10 |
| TiO$_2$ | 1.00 |
| TOTAL | 100.00 |

In this example, as in the examples 5, 6 and 7 below, the use of flavorings was avoided.

2. Preparation of the Solution

First, isomalt GS (1,6-GPS-enriched mixture of 1,1-GPM and 1,6-GPS having a 1,6-GPS content >57%), sweeteners and water are stirred and heated until a crystal-free solution is present (70-80° C.). Thereafter, the supply of energy is shut off. Then, a gum arabic solution, TiO$_2$ and also the apatite-gelatin composite particles produced in example 1 are added and the mixture is stirred until it is homogeneous. The final temperature of the solution is about 50° C. During the entire dragee-coating period, the solution is circulated or stirred and held at about 45 to 55° C. When automatic systems are used, the piping must be heatable accordingly.

3. Dragee-Coating Process

Since certain centers during the first four dragee-coating cycles have a tendency to stickiness and on account of this to formation of agglomerates, after the solution has been added and distributed, after sufficient distribution of the solution prepared on the surface of the chewing gum cores, dusting with isomalt ST-PF, if appropriate in combination with apatite-gelatin composite particles is carried out.

In the first dragee-coating cycle, an amount of 10-12 ml or 12.5-15.6 g of solution/kg of chewing gum cores is applied, so that the centers are completely moist. Thereafter, the solution is thoroughly distributed. To avoid agglomerate formation, the chewing gum cores are dusted with sieved isomalt ST-PF (10-15 g/kg of chewing gum cores). After sufficient distribution, drying is carried out.

In the following three cycles, the amount of solution is reduced to 7-10 ml and the amount of powder to 9-13 g/kg of chewing gum cores. During the further dragee-coating process, the amount of solution/phase is increased until the desired weight of the dragee layer is virtually achieved. In the last two to three phases, the dragee-coated chewing gums are smoothed by reduction of the amount of solvent and longer distribution pauses. To achieve a good crispiness and lasting gloss, a jogging step is carried out at about 3×4 rpm using dry air over a period of 15 to 30 minutes. The dust which is formed by the intensive drying is bound by an application of solution. Thereafter, a drying step is carried out without feed of dry air, until the surface is dry and dust-free. Thereafter, a polishing process is carried out, approximately 15 g of carnauba wax being crushed between the dragees. To avoid the dragee coat from breaking off during the polishing process, the speed of rotation of the drum is set very low at the start of the polishing process. As soon as the polishing medium is well distributed, the speed of rotation is increased.

In a modification of the method, a solution of isomalt GS, sweeteners, gum arabic solution, TiO$_2$, flavorings and colorings is prepared. To this solution is then added a portion of the amount provided of the apatite-gelatin composite particles. This solution is then, as described above, applied to the chewing gum cores. Thereafter, dusting is carried out using a powder mixture which comprises isomalt ST-PF and the remaining amount of the apatite-gelatin composite particles to be incorporated into the dragee layer. In a further modification of the method, a solution is first prepared and applied to the chewing gum cores, which solution comprises isomalt GS, sweeteners, gum arabic solution, TiO$_2$, flavorings and colorings, but not the apatite-gelatin composite particles. After the application of this solution to the chewing gum cores, dusting is then carried out using either a powder mixture of isomalt ST-PF and the apatite-gelatin composite particles to be incorporated into the dragee layer, or only the apatite-gelatin composite particles (as what is termed "dry charge") in dry form.

The method can be used not only for conventional open dragee coating, but also for closed dragee-coating systems.

In this method also, a pregumming step can be carried out, as described in example 3.

Example 5

Dragee Coating of Chewing Gum Cores with an Isomalt GS Suspension

Dragees having a coat proportion of 33% by mass are produced.

1. Formula for Dragee Layer

| RAW MATERIALS | % |
| --- | --- |
| ISOMALT GS | 43.65 |
| Apatite-gelatin composite according to example 1 | 1.00 |
| Water | 28.00 |
| Aspartame | 0.05 |
| Acesulfame K | 0.05 |
| Gum arabic 50% | 4.10 |
| ISOMALT ST-PF | 22.15 |
| TiO$_2$ | 1.00 |
| Total | 100.00 |

2. Preparation of the Suspension

Isomalt GS, sweeteners and water are stirred and heated until a crystal-free solution is present (70-80° C.). Thereafter, the energy supply is shut off. Then, a gum arabic solution, apatite-gelatin composite particles, isomalt ST-PF and TiO$_2$ are added and the mixture is stirred until a homogeneous mass is present. The final temperature of the suspension is about 40° C. During the entire dragee-coating period, the suspension is circulated or stirred and held at about 40 to 45° C.

3. Dragee-Coating Process

In the first cycle, an application rate of 10-12 ml, or 12.5-15.6 g of suspension/kg of chewing gum cores is applied, so that the centers are completely moistened. The suspension is then thoroughly distributed. To avoid agglomerate formation, the chewing gum cores are dusted with sieved isomalt ST-PF (10-15 g/kg of chewing gum cores). Then drying is performed. In the following three cycles, the amount of suspension is reduced to 7-10 ml and the amount of powder to 9-13 g/kg of chewing gum cores. During the further dragee-coating process, the amount of suspension/phases is increased until the desired weight of the dragee coat is reached. In the last two to three phases, the dragee-coated chewing gums are smoothed by reduction of the amount of suspension and longer distribution pauses. Good crispiness and lasting glossiness are achieved by means of a jogging step at about 3×4 rpm using dry air over a period of 15 to 30 minutes. The dust which is formed by the intensive drying is bound by a last application of suspension. Thereafter, drying is performed without feed of dry air until the surface is dry and dust-free. Thereafter, a polishing process is carried out, approximately 15 g of carnauba wax being crushed between the dragees.

Here also, the method can be modified by adding only a portion of the total amount provided of the apatite-gelatin composite particles to the suspension and using the remaining amount of the apatite-gelatin composite particles for dusting.

Obviously, the total amount of the apatite-gelatin composite particles to be incorporated into the dragee layer can also be used entirely for dusting.

Here also, pregumming can be carried out, as described in example 3.

Example 6

Dragee Coating of Chewing Gum Cores with Isomalt ST Solution

Dragees having a coat proportion of 33% by mass are produced.

1. Formula for Dragee Layer

| RAW MATERIALS | % |
| --- | --- |
| ISOMALT ST-M | 65.00 |
| Apatite-gelatin composite according to example 1 | 1.00 |
| Water | 28.80 |
| Aspartame | 0.05 |
| Acesulfame K | 0.05 |
| Gum arabic 50% | 4.10 |
| TiO$_2$ | 1.00 |
| TOTAL | 100.00 |

2. Preparation of the Solution

Isomalt ST-M, sweeteners and water are stirred and heated until a crystal-free solution is present (70-80° C.). Thereafter, the energy supply is shut off. A gum arabic solution, apatite-gelatin composite particles and TiO$_2$ are added and the mixture is stirred until a homogeneous mass is present. The final temperature of the solution is about 60° C. During the entire dragee-coating period, the solution is circulated or stirred and held at about 60-70° C.

3. Dragee-Coating Process

In the first cycle, an application rate of 10-12 ml or 12.5-15.6 g of solution/kg of chewing gum cores is applied, the centers being completely moistened. Thereafter, the solution is thoroughly distributed. To avoid agglomerate formation, the centers are dusted with sieved isomalt ST-PF (10-15 g/kg of chewing gum cores). Distribution and drying then take place.

In the next three cycles, the amount of solution is reduced to 7-10 ml and the amount of powder to 9-13 g/kg of chewing gum cores. During the further dragee-coating process, the amount of solution/phase is increased until the desired weight of the dragee coat is virtually reached. In the last two to three phases, the dragee-coated chewing gums are smoothed by reduction of the amount of solution and longer distribution pauses. By carrying out a jogging step at about 3×4 rpm with dry air over a period of 15 to 30 minutes, a good crispiness and lasting glossiness are achieved. The dust which is formed by the intensive drying is bound by an application of solution. Thereafter, drying is performed without feed of dry air until the surface is dry and dust-free. Thereafter, a polishing process is carried out, approximately 15 g of carnauba wax being crushed between the dragees. To avoid the coat from breaking off during the polishing process, the speed of rotation of the drum is set relatively low at the start of the polishing process. As soon as the polishing medium is well distributed, the speed of rotation is increased.

The method can be modified by adding only a portion of the total amount provided of the apatite-gelatin composite particles to the solution and using the remaining amount of the apatite-gelatin composite particles for dusting. In a further modification, the total amount of the apatite-gelatin composite particles to be incorporated into the dragee layer can be entirely used for dusting.

Here also, pregumming can be carried out, as described in example 3.

Example 7

Dragee Coating of Chewing Gum Cores with Isomalt ST Suspension

Dragees having a coat proportion of 33% by mass are produced.

1. Formula for the Dragee Layer

| RAW MATERIALS | % |
| --- | --- |
| ISOMALT ST-M | 43.65 |
| Apatite-gelatin composite according to example 1 | 1.00 |
| Water | 28.00 |
| Aspartame | 0.05 |
| Acesulfame K | 0.05 |
| Gum arabic 50% | 4.10 |
| TiO$_2$ | 1.00 |
| TOTAL | 100.00 |

2. Preparation of the Suspension

Isomalt ST-M, sweeteners and water are stirred and heated until a crystal-free solution (70-80° C.) is present. Thereafter, the energy supply is shut off. The gum arabic solution, isomalt ST-PF, the apatite-gelatin composite particles produced according to example 1 and TiO$_2$ are added and the mixture is stirred until a homogeneous mass is present. The final temperature of the suspension is about 55° C. For an entire dragee-coating period, the solution is circulated or stirred and held at about 50-60° C.

3. Dragee-Coating Process

In the first cycle, an application rate of 10-12 ml or 12.5-15.6 g of suspension/kg of chewing gum cores is applied, the centers being completely moistened. Thereafter, the suspension is thoroughly distributed. To avoid agglomerate formation, the centers are dusted with sieved isomalt ST-PF (10-15 g/kg of chewing gum cores). Distribution and drying are then carried out. In the next three cycles, the amount of suspension is reduced to 7 to 10 ml and the amount of powder to 9-13 g/kg of chewing gum cores. During the further dragee-coating process, the amount of suspension/phase is increased until the desired weight of the dragee coat is virtually completely reached. In the last 2-3 phases, the dragee-coated chewing gums are smoothed by reduction of the amount of suspension and longer distribution pauses. A jogging step is then carried out at approximately 3×4 rpm with dry air over a period of 15 to 30 minutes. The dust which is formed by the intensive drying is bound by a last application of suspension. Thereafter, drying is performed without feed of dry air until the surface is dry and dust-free. Thereafter, a polishing process is carried out, approximately 15 g of carnauba wax being crushed between the dragees.

The method can be modified by adding only a portion of the total amount provided of the apatite-gelatin composite particles to the suspension and using the remaining amount of the apatite-gelatin composite particles for dusting. In a further modification, the total amount of the apatite-gelatin composite particles to be incorporated into the dragee layer can be used completely for dusting.

Here also, a pregumming step, as described in example 3, can be carried out.

Example 8

Production of Chewing Gum Dragees by Means of a Semi-automatic Dragee Plant

Chewing gum centers from Gum Base, Italy were furnished with a dragee coat which comprised 1% apatite-gelatin composite particles.

Table 2 shows an overview of the dragee coating carried out with different sweeteners.

TABLE 2

Overview of the dragee coating using different sugars or sugar alcohols

| Raw material | Medium[1] | $T_A$ [° C.] | DM [%] |
|---|---|---|---|
| Sucrose | Solution | 60 | 72 |
| Maltitol | Solution[3] | 60 | 71 |
| Maltitol | Solution[3] | 60 | 72 |
| Maltitol | Solution[3] | 60 | 71 |
| Maltitol | Solution[3] | 60 | 69 |
| Maltitol | Solution[3] | 60 | 71 |
| Maltitol | Suspension[2] | 45 | 74 |
| Isomalt ST | Solution[4] | 70 | 67 |
| Isomalt ST | Suspension[2] | 65 | 67 |
| Isomalt GS | Solution[4] | 50 | 67 |
| Isomalt GS | Suspension[2] | 40 | 67 |
| Isomalt GS | Solution[4] | 65 | 72 |
| Isomalt GS | Solution[4] | 55 | 67 |
| Isomalt GS | Solution[4] | 55 | 67 |
| Isomalt GS | Suspension[2] | 47 | 72 |

[1]all media comprise 2% gum arabic and 1% apatite-gelatin composite
[2]ratio of dissolved polyol to solid is 2:1
[3]comprises 0.5% titanium dioxide
[4]comprises 1% titanium dioxide Preparation of the Dragee-Coating Media The dragee-coating media were prepared in a stainless steel cooking pot (V=14 l). The preparation is carried out in a systematized manner for reproducible production of dragee-coating media, but in a separately defined manner for solution and suspension. Firstly, the required amount of demineralized water is heated (70° C. for isomalt GS formulas and 80° C. for isomalt ST formulas). The amount of sugar alcohol to be dissolved is added mixed with any solid ingredients used, for example gum arabic. In the preparation of a solution, the entire amount of polyol is dispersed in in portions and dissolved. Under permanent agitation using a propeller agitator at a maximum 250 min$^{-1}$, driven by a Eurostar stirrer from IKA, the mixture cools to 5-7 K >working temperature ($T_A$). In the preparation of a suspension, the powder (disperse phase) is added in portions. Before this addition, the hot plate is turned off so that not too much of the solid which has been dispersed in likewise passes into solution. The cooling of the system to the working temperature is supported by the enthalpy of solution of the solid. The temperature is monitored using a Pt 100 probe from TESTOTHERM. The suspension has a yellowish-milky color, while the solution is clear-yellow. Finally, the coloring and the apatite-gelatin-composite particles are added. After their complete dispersion, the dragee-coating medium is transferred to the preheated reservoir vessel of the coater via a sieve. The coater metering device is then calibrated.

Dragee-Coating Plant Used

For the dragee coating, a DRIACOATER Vario 500/600 from DRIAM is used. This is a semiautomatic dragee-coating plant consisting of a computer unit, a heating, metering and air-feed system and a perforated nonagonal drum. Peripherals include a unit for conditioning the drying air. The working volume of the DRC Vario 500/600 is 10 kg for chewing gum cores.

A membrane metering pump transports the dragee-coating medium from the reservoir vessel LT bi 10 to the two pneumatically operated single-fluid nozzles from SPRAYING SYSTEM type 1/8 JJ AUH-SS. The stability and height of the transport pressure and thus the resultant spraying area is dependent on the viscosity of the dragee-coating medium and on the nozzle mouthpiece used. Principally, the mouthpiece type TEEJET 9501, d=0.66 mm was used. At insufficient pressures, the mouthpiece 800067 having a diameter of 0.53 mm is used. The entire spray arm, its supply lines and the reservoir vessel are held under temperature control by a double-shell system. The dragee-coating medium is kept in motion in the reservoir vessel under constant stirring.

The available air guidance system of the coater makes possible two variants of the drying of the material: cocurrent flow drying in which the air has the same direction as the spray jet, or countercurrent flow drying in which the air flows through the material via the perforated drum wall. All dragee coatings were carried out in this example using countercurrent flow drying. The air used for drying is conditioned in advance, the air in the temperature control unit first being cooled or heated to the required temperature. Thereafter, the desired amount of water is fed into the temperature-controlled air by means of steam. The air thus treated can then be used as conditioned air (desired dew point) for drying.

Via the process control computer, using the software OCTOPUS 3000, programming and storage of dragee-coating programs are ensured. Furthermore, continuously determined measurements, for example exhaust air temperature and exhaust air moisture, are displayed.

Dragee-Coating

First, as described above, the dragee-coating medium is produced. In the interim, the chewing gum cores are freed from talcum and smoothed in the rotating and ventilated drum. After transfer of the dragee-coating medium to the reservoir vessel, the metering system is calibrated.

Table 3 shows the parameters used for the dragee coating.

TABLE 3

Working conditions for dragee coating using DRC Vario 500/600

| Parameter | Setting |
|---|---|
| Drum speed [min$^{-1}$] | 20 |
| Volumetric flow rate of the drying air [m$^3$/min] | 5 |
| Dew point [° C.] | −2 to 0 |
| Temperature of the drying air [° C.] | 25 |
| Differential pressure in the drum [mbar] | 4 |
| Batch size (cores) [kg] | 8 |

During the first three cycles, after half the time in the distribution phase, approximately 70 g of powder of the sugar replacer used is dispersed over the moist cores, since the tendency to sticking together at that time is very strong.

Furthermore, cores adhering during these cycles can be removed from the drum interior wall.

Dragees having a coat proportion of 33% by mass are produced. All dragee coatings are terminated by a polishing phase, approximately 15 g of carnauba wax being crushed between the dragees.

The invention claimed is:

1. A chewing gum coated by at least one layer, said layer comprising a coating material which is a composite of a slightly water-soluble calcium salt and a protein component, which salt is selected from the group consisting of fluoroapatite, carbonate-containing nonstoichiometric apatite, hydroxyapatite and fluorine-doped hydroxyapatite, wherein the slightly water-soluble calcium salt has a particle size less than 1000 nm.

2. The chewing gum of claim 1, wherein the slightly water-soluble calcium salt has a particle size of 5 to 300 nm.

3. The chewing gum of claim 1, wherein the slightly water-soluble calcium salt is present in the form of rod-shaped crystals.

4. The chewing gum of claim 1, wherein the coating layer comprises 0.001 to 5% by weight of said coating material.

5. The chewing gum of claim 1, wherein the protein component is selected from the group consisting of gelatin, caseine and hydrolyzates thereof.

6. The chewing gum of claim 1 wherein said coating material is coated by one or more surface-modification agents.

7. The chewing gum of claim 1 wherein at least one coating layer is a dragee-coated layer.

8. The chewing gum of claim 1, wherein the chewing gum comprises at least one sugar.

9. The chewing gum of claim 8, wherein at least one of the chewing gum and the coating layer comprises, as a sweetener, at least one of sucrose, invert liquid sugar, invert sugar syrup, glucose, glucose syrup, polydextrose, tagatose, trehalose, trehalulose, maltose, lactose, fructose, leucrose, palatinose, condensed palatinose, hydrogenated condensed palatinose, and mixtures thereof.

10. The chewing gum of claim 9 wherein at least one of the chewing gum and the coating layer comprises, as an additional sweetener, at least one of fructooligosaccharides, lactitol, sorbitol, xylitol, mannitol, maltitol, erythritol, 6-O-α-D-glucopyranosyl-D-sorbitol (1,6-GPS), 1-O-α-D-glucopyranosyl-D-sorbitol (1,1-GPS), 1-O-α-D-glucopyranosyl-D-mannitol (1,1-GPM) and mixtures thereof.

11. The chewing gum of claim 1, wherein the chewing gum is substantially sugar-free.

12. The chewing gum of claim 11, wherein the chewing gum and the coating layer comprise, as a sweetener, at least one of fructooligosaccharides, lactitol, sorbitol, xylitol, mannitol, maltitol, erythritol, 6-O-α-D-glucopyranosyl-D-sorbitol (1,6-GPS), 1-O-α-D-glucopyranosyl-D-sorbitol (1,1-GPS), 1-O-α-D-glucopyranosyl-D-mannitol (1,1-GPM) and mixtures thereof.

13. The chewing gum of claim 10 wherein the mixture is selected from the group consisting of an equimolar or virtually equimolar mixture of 1,6-GPS and 1,1-GPM (isomalt), a mixture of 1,6-GPS, 1,1-GPS and 1,1-GPM, a 1,6-GPS-enriched mixture of 1,6-GPS and 1,1-GPM having a 1,6-GPS content of 57% by weight to 99% by weight and a 1,1-GPM content of 43% by weight to 1% by weight, a 1,1-GPM-enriched mixture of 1,6-GPS and 1,1-GPM having a 1,6-GPS content of 1% by weight to 43% by weight and a 1,1-GPM content of 57% by weight to 99% by weight, and a syrup consisting of a mixture of hydrogenated starch hydrolyzate syrup and isomalt syrup or isomalt powder, the dry matter of the syrup consisting of 7-52% (weight/weight) 1,6-GPS, 24.5-52% (weight/weight) 1,1-GPM, 0-52% (weight/weight) 1,1-GPS, 0-13% (weight/weight) sorbitol, 2.8-13.8% (weight/weight) maltitol, 1.5-4.2% (weight/weight) maltotriitol and 3.0-13.5% (weight/weight) higher polyols.

14. The chewing gum of claim 1, wherein at least one of the chewing gum and the coating layer comprises one or more intense sweeteners.

15. The chewing gum of claim 14, wherein the intense sweetener is selected from the group consisting of cyclamate, saccharin, aspartame, glycyrrhizin, neohesperidin dihydrochalcone, stevioside, thaumatin, monellin, acesulfame, alitame, sucralose, and mixtures thereof.

16. The chewing gum of claim 7 comprising from 2 to about 100 dragee-coated layers.

17. The chewing gum of claim 16, wherein each said dragee-coated layer comprises the same sweetener(s).

18. The chewing gum of claim 16, wherein each said dragee-coated sweetener layer comprises a different sweetener.

19. The chewing gum of claim 16, wherein each said individual dragee-coated layer is comprised of the same composite.

20. The chewing gum of claim 16, wherein each said individual dragee-coated layer is comprised of a different composite.

21. The chewing gum of claim 1, further comprising at least one fluoride salt.

22. The chewing gum of claim 1, further comprising at least one material selected from the group consisting of flavorings and fillers.

23. A method for producing the chewing gum of claim 1, said method comprising producing a chewing gum core and coating the chewing gum core with at least one layer which comprises a composite of a slightly water-soluble calcium salt and a protein component, which salt is selected from the group consisting of fluoroapatite, carbonate-containing nonstoichiometric apatite, hydroxyapatite and fluorine-doped hydroxyapatite, wherein the slightly water-soluble calcium salt has a particle size less than 1000 nm.

24. The method of claim 23, wherein the chewing gum core is coated by at least one hard dragee-coating step.

25. The method of claim 24, wherein the hard dragee-coating step comprises applying a solution or suspension which comprises at least one sweetener and the composite, and drying the solution or suspension.

26. The method of claim 23, wherein the chewing gum core is coated, by means of at least one soft dragee-coating step.

27. The method of claim 26, wherein the soft dragee-coating step comprises applying a solution or suspension which comprises at least one sweetener, and then dusting the applied solution or suspension with a sweetener powder.

28. The method of claim 27, wherein the applied solution or suspension comprises at least a portion of the total amount of the composite.

29. The method of claim 27, wherein the sweetener powder comprises at least a portion of the total amount of the composite.

30. The method of claim 24, wherein hard dragee-coating steps or soft dragee-coating steps are repeated several times.

31. The method of claim 23, wherein the calcium salt has a particle size of 5 to 300 nm.

32. The method of claim 23, wherein the coating layer comprises 0.001 to 5% by weight of the composite.

33. A method for improving dental hygiene in a subject in need thereof, which comprises chewing, by said subject, of the chewing gum of claim 1.

34. A method for mineralizing the tooth enamel of a subject in need thereof, which comprises chewing, by said subject, of the chewing gum of claim 1.

35. A method for mineralizing the dentine of a subject in need thereof, which comprises chewing, by said subject, of the chewing gum of claim 1.

36. The chewing gum of claim 4, wherein the coating layer comprises 0.01 to 2% by weight of said coating material.

37. The chewing gum of claim 5, wherein the protein component is gelatin.

38. The method of claim 32 wherein the coating layer comprises 0.01 to 2% by weight of the composite.

* * * * *